(12) United States Patent
Choi et al.

(10) Patent No.: US 10,463,890 B2
(45) Date of Patent: Nov. 5, 2019

(54) METHOD FOR PREPARING BROCCOLI WITH INCREASED SULFORAPHANE CONTENT AND USE OF BROCCOLI PREPARED THEREBY

(71) Applicant: BKBIO CO., LTD., Jeju-do (KR)

(72) Inventors: Hyuk Joon Choi, Gyeonggi-do (KR); Kyoungsook Choi, Seoul (KR); Jung-Ky Jeong, Seoul (KR); Geon Kim, Incheon (KR); Dong-Un Lee, Seoul (KR)

(73) Assignee: BKBIO CO., LTD., Jeju-Do (KR)

( * ) Notice: Subject to any disclaimer, the term of this patent is extended or adjusted under 35 U.S.C. 154(b) by 334 days.

(21) Appl. No.: 15/303,779

(22) PCT Filed: Apr. 3, 2015

(86) PCT No.: PCT/KR2015/003340
§ 371 (c)(1),
(2) Date: Oct. 13, 2016

(87) PCT Pub. No.: WO2015/160124
PCT Pub. Date: Oct. 22, 2015

(65) Prior Publication Data
US 2017/0042793 A1    Feb. 16, 2017

(30) Foreign Application Priority Data

Apr. 14, 2014 (KR) .................. 10-2014-0044150
Apr. 2, 2015 (KR) .................. 10-2015-0046670

(51) Int. Cl.
| | | |
|---|---|---|
| *A61Q 19/00* | (2006.01) | |
| *A23B 7/015* | (2006.01) | |
| *A23K 20/10* | (2016.01) | |
| *A23L 33/10* | (2016.01) | |
| *A23K 10/30* | (2016.01) | |
| *A61K 36/31* | (2006.01) | |
| *A61K 8/9783* | (2017.01) | |

(52) U.S. Cl.
CPC ............. *A61Q 19/00* (2013.01); *A23B 7/015* (2013.01); *A23K 10/30* (2016.05); *A23K 20/10* (2016.05); *A23L 33/10* (2016.08); *A61K 8/9783* (2017.08); *A61K 36/31* (2013.01); *A61K 2236/30* (2013.01); *A61K 2800/92* (2013.01)

(58) Field of Classification Search
CPC ........ A23B 7/015; A23K 10/30; A23K 20/10; A23L 33/10; A61K 2236/30; A61K 2800/92; A61K 36/31; A61K 8/9783; A61K 8/46; A61K 8/97; A61Q 19/00; A61Q 19/10
See application file for complete search history.

(56) References Cited

U.S. PATENT DOCUMENTS 8,147,879 B2    4/2012 Ngadi et al.

FOREIGN PATENT DOCUMENTS

| | | |
|---|---|---|
| JP | 2013531052 | 8/2013 |
| KR | 1020000016830 | 3/2000 |
| KR | 1008462150000 | 11/2005 |
| KR | 1009467270000 | 3/2010 |
| KR | 1020100116759 | 11/2010 |
| KR | 1010563520000 | 8/2011 |
| KR | 101171846000 | 8/2012 |

OTHER PUBLICATIONS

Subedi L, et al "Sulforaphane-Enriched Broccoli Sprouts Pretreated by Pulsed Electric Fields Reduces Neuroinflammation and Ameliorates Scopolamine-Induced Amnesia in Mouse Brain through Its Antioxidant Ability via Nrf2-HO-1 Activation" Oxid.Med.Cell. Longev.,2019,2019,1-19;doi:10.1155/2019/3549274. (Year: 2019).*
Aguilo-Aguayo I, et al, J. Sci. Food and Agric.,Oct. 2014,95(9);doi:10.1002/jsfa.6891. (Year: 2014).*
Frandsen, et al., "Effects of Novel Processing Techniques on Glucosinolates and Membrane Associated Myrosinases in Broccoli", Pol. J. Food Nutr. Sci., vol. 64, No. 1, pp. 17-25, 2014.

* cited by examiner

*Primary Examiner* — Aaron J Kosar
(74) *Attorney, Agent, or Firm* — Duane Morris LLP; Gregory M. Lefkowitz; Jason M. Nolan

(57) ABSTRACT

Disclosed is a method for preparing broccoli with increased sulforaphane content using high-voltage pulsed electric field treatment. According to the method, broccoli with increased sulforaphane content can be eaten raw or can be chopped to appropriate sizes before eating without the need to crush the broccoli. In addition, sulforaphane can be extracted from the broccoli with increased sulforaphane content. The broccoli with increased sulforaphane content and the sulforaphane extract produced therefrom can be used as an active ingredient of a food, feed or cosmetic composition to exhibit the activities of sulforaphane, including antioxidative and anti-inflammatory activities.

18 Claims, 3 Drawing Sheets

Comparative Example 1     Example 1

Comparative Example 1     Example 1

Comparative Example 1            Example 1

Comparative Example 1            Example 1

METHOD FOR PREPARING BROCCOLI WITH INCREASED SULFORAPHANE CONTENT AND USE OF BROCCOLI PREPARED THEREBY

CROSS-REFERENCE TO RELATED APPLICATIONS

This application is a § 371 national stage entry of International Application No. PCT/KR2015/003340, filed on Apr. 3, 2015, which claims priority to South Korean Patent Application No. 10-2014-0044150, filed on Apr. 14, 2014, and South Korean Patent Application No. 10-2015-0046670, filed on Apr. 2, 2015, the entire contents of which are incorporated herein by reference.

FIELD OF THE INVENTION

The present invention relates to a method for preparing broccoli with increased sulforaphane content, broccoli prepared by the method, and a food, feed or cosmetic composition including the broccoli.

The present invention also relates to a method for producing sulforaphane from broccoli prepared by the method for preparing broccoli with increased sulforaphane content and a food, feed or cosmetic composition including sulforaphane produced by the method.

DESCRIPTION OF THE RELATED ART

Sulforaphane is an anticancer and antioxidant substance found in vegetables of the family Brassicaceae and is a kind of isothiocyanate produced by enzymatic hydrolysis of glucosinolates as secondary metabolites found in vegetables of the family Brassicaceae. Fresh broccoli contains large amounts of glucosinolates and a relatively very small amount of sulforaphane. However, when fresh broccoli is pulverized into a powder, bioconversion of glucosinolates to sulforaphane occurs, leading to a considerable increase in the sulforaphane content of the powder. Accordingly, a broccoli extract from the powder contains a significantly increased amount of sulforaphane compared to the fresh broccoli. It is known that such a broccoli extract induces the expression of antioxidant enzymes to repress genetic modifications caused by oxidative damage, suppresses the growth of *Helicobacter pylori* known as responsible for the occurrence of gastric cancer, and inhibits the production of gastric cancer by carcinogenic substances in animal experiments.

Broccoli is a vegetable that is often used as a raw material for some processed foods but is mostly consumed in the form of salads. In the case where a broccoli salad is prepared, the broccoli is generally blanched in water vapor or boiling water to provide a soft chewing texture of the broccoli. However, heating of fresh broccoli causes degradation of glucosinolates, and as a result, the content of glucosinolates decreases, leading to a reduction in sulforaphane content.

High-voltage pulsed electric field treatment is a known process for non-thermal sterilization against spoilage microorganisms to extend the shelf life of vegetable products while with less damage to the flavor of the products (Korean Patent Publication No. 2000-0016830). High-voltage pulsed electric field treatment is also known as a pretreatment process for the enhancement of extraction yield (Korean Patent Publication No. 10-2010-0052065). However, there has been no report on the use of high-voltage pulsed electric field treatment for broccoli processing to enhance the content of sulforaphane.

DETAILED DESCRIPTION OF THE INVENTION

Technical Problem

It is an object of the present invention to provide a method for preparing broccoli with increased sulforaphane content using high-voltage pulsed electric field treatment by which broccoli with increased sulforaphane content can be eaten raw or can be chopped to appropriate sizes before eating without the need to crush the broccoli, broccoli prepared by the method, and a food, feed or cosmetic composition including the broccoli.

It is another object of the present invention to provide a method for producing sulforaphane from broccoli prepared by the method for preparing broccoli with increased sulforaphane content using high-voltage pulsed electric field treatment and a food, feed or cosmetic composition including sulforaphane produced by the method.

Technical Solution

One aspect of the present invention provides a method for preparing broccoli with increased sulforaphane content, including: introducing broccoli into a batch or continuous type vessel containing a liquid medium; and treating the liquid medium 1 to 50 times with a high-voltage pulsed electric field of 0.1 to 200 kV/cm at a frequency of 1 to 100 Hz for 0.1 to 300 seconds.

The high-voltage pulsed electric field treatment is preferably performed at 0.2 to 20 kV/cm for 1 to 50 seconds.

Preferably, the broccoli being introduced intact into the vessel is either intact or is chopped into pieces, the broccoli being not subject to pulverization or trituration The liquid medium is preferably water, ethanol or a mixture thereof.

The liquid medium may further contain an organic acid, such as acetic acid, citric acid or lactic acid, or an inorganic salt, such as salt.

Preferably, the broccoli having undergone the high-voltage pulsed electric field treatment is subjected to drying, pulverization, pulverization after drying, or drying after pulverization.

A further aspect of the present invention provides broccoli with increased sulforaphane content that is prepared by the method and whose sulforaphane content after high-voltage pulsed electric field treatment is higher by at least 30%, preferably at least 50%, more preferably 100% to 1000%, than its original sulforaphane content before the treatment.

Fresh broccoli before high-voltage pulsed electric field treatment typically contains 30 mg to 70 mg of sulforaphane, with an average of about 40 mg, per 100 g of dry broccoli. Broccoli loses most of its sulforaphane content upon blanching, the most common pretreatment process, before eating. According to the present invention, the sulforaphane content of the broccoli after the high-voltage pulsed electric field treatment is from 100 mg to 200 mg per 100 g of dry broccoli and is 1.5 to 8 times higher than that of the intact broccoli before the treatment.

Another aspect of the present invention provides a method for producing a sulforaphane extract from the broccoli with increased sulforaphane content.

The sulforaphane extract may be produced using water, an organic solvent or a mixture thereof as an extraction solvent. There is no particular restriction on the kind of the organic solvent and the mixing ratio between the water and the organic solvent.

For example, the organic solvent may be selected from the group consisting of a lower alcohol, hexane, acetone, ethyl acetate, chloroform, diethyl ether, and mixtures thereof. The lower alcohol may be a $C_1$-$C_6$ alcohol, for example, methanol, ethanol, propanol, butanol, n-propanol, iso-propanol, n-butanol, 1-pentanol, 2-butoxyethanol or ethylene glycol. Examples of other organic solvents include: polar solvents, such as acetic acid, dimethylformamide (DMF), and dimethyl sulfoxide (DMSO); and non-polar solvents, such as acetonitrile, ethyl acetate, methyl acetate, fluoroalkanes, pentane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride, and tetrahydrofuran (THF).

Sulforaphane may be extracted from the broccoli with increased sulforaphane content using water, ethanol, methanol or two or more solvents selected from water, ethanol, and methanol.

The sulforaphane extract may be produced by extracting the broccoli with increased sulforaphane content with water at 40 to 100° C. for 2 to 48 hours. Preferably, the sulforaphane extract is produced by extracting the broccoli with increased sulforaphane content with water containing at least one enzyme selected from the group consisting of cellulase, viscozyme, alcalase, and pepsin at 40 to 55° C. for 2 to 24 hours. The enzyme is added to enhance the extraction efficiency of the water soluble ingredient by water extraction.

The ethanol extract or the aqueous ethanol extract may be produced by extracting the broccoli with increased sulforaphane content with ethanol or an aqueous solution of 35 to 75% by volume of ethanol at 20 to 60° C. for 2 to 36 hours, preferably at 40 to 50° C. for 2.5 to 6 hours. More preferably, the aqueous ethanol extract is produced by extracting the broccoli with increased sulforaphane content with an aqueous solution of 70% by volume of ethanol at 45° C. for 3 hours.

As used herein, the term "extract" is intended to include fractionation products obtained by further fractionation of the extract. That is, the sulforaphane extract includes not only extracts obtained using the above-described extraction solvents but also sulforaphane concentrates obtained by further purification of the extracts. The sulforaphane extract of the present invention is also intended to include fractions obtained by passing the extracts or fractionation products through ultrafiltration membranes having a specific cut-off molecular weight, and fractions obtained through various additional purification processes, for example, various chromatography separation processes (those depending on size, charge, hydrophobicity or affinity).

Another aspect of the present invention provides a food composition including the broccoli with increased sulforaphane content or a food composition including a sulforaphane extract produced by the method.

The broccoli with increased sulforaphane content or the sulforaphane extract produced therefrom according to the present invention may be used as an active ingredient in a health functional food or a general food. In this case, the broccoli or the sulforaphane extract of the present invention may be added without further processing or may be used together with other foods or food ingredients in accordance with methods known in the art. The amount of the active ingredient may be suitably determined according to its intended purpose, such as prophylactic, health care or therapeutic purpose.

When it is intended to produce a food or beverage, the broccoli or the sulforaphane extract of the present invention is typically added in an amount of 15 parts by weight or less, preferably 10 parts by weight or less, based on 100 parts by weight of the raw materials of the food or beverage. In the case where the food or beverage is taken for a long time for the purpose of health and hygiene or health care, the amount of the broccoli or the sulforaphane extract may be adjusted to less than the lower limit defined above. The food composition of the present invention is free from problems associated with safety because it uses the natural product or the extract thereof. Accordingly, the broccoli or the sulforaphane extract may also be used in an amount exceeding the upper limit defined above.

There is no particular restriction on the kind of the food. Examples of foods that may be added with the broccoli or the sulforaphane extract include all common foods, such as meats, sausages, breads, chocolates, candies, snacks, cookies, pizzas, instant noodles, other noodles, chewing gums, dairy products including ice creams, soups, beverages, teas, drinks, alcoholic beverages, and vitamin complexes.

The health functional food may be a beverage food. In this case, the beverage food may contain one or more additional ingredients, such as flavoring agents or natural carbohydrates, like general beverages. The natural carbohydrates may be monosaccharides, such as glucose and fructose, disaccharides, such as maltose and sucrose, polysaccharides, such as dextrin and cyclodextrin, and sugar alcohols, such as xylitol, sorbitol, and erythritol. The beverage food may contain one or more sweetening agents. As the sweetening agents, there may be used, for example, natural sweetening agents, such as thaumatin and stevia extract, and synthetic sweetening agents, saccharine and aspartame. The total weight of the natural carbohydrates may be from about 0.01 to about 0.04 g, preferably from about 0.02 to about 0.03 g, based on 100 mL of the functional food.

The food composition of the present invention may be used for ameliorating or preventing inflammation or cancer due to its antioxidant activity. In this case, the food composition of the present invention may further contain one or more additives selected from nutrients, vitamins, electrolytes, flavoring agents, coloring agents, pectic acid and its salts, alginic acid and its salts, organic acids, protective colloidal thickeners, pH adjusting agents, stabilizers, preservatives, glycerin, alcohols, and carbonating agents for carbonated drinks. The food composition of the present invention may further contain flesh for the production of natural fruit juices, fruit juice beverages, and vegetable beverages. Such ingredients may be used independently or as a mixture thereof. The proportions of such additives are not limited but are typically selected from the range of 0.01 to 0.1 parts by weight, based on 100 parts by weight of the composition of the present invention.

Another aspect of the present invention provides a feed composition including the broccoli with increased sulforaphane content or a feed composition including a sulforaphane extract produced by the method. The feed composition may be a feed or a feed additive.

The feed composition may further include one or more additives selected from organic acids, such as citric acid, fumaric acid, adipic acid, lactic acid, and malic acid, phosphoric acid salts, such as sodium phosphate, potassium phosphate, dihydrogen pyrophosphate, and polyphosphate, and natural antioxidants, such as polyphenol, catechin, alpha-tocopherol, rosemary extract, vitamin C, green tea extract, licorice extract, chitosan, tannic acid, and phytic acid.

Examples of auxiliary ingredients suitable for use in the feed composition include adjuvants, such as amino acids, inorganic salts, vitamins, antibiotics, antibacterial substances, antioxidant/antifungal enzymes, active and microbial agents. Examples of main ingredients suitable for use in the feed composition include: cereals, for example, crushed or powdered wheat, oat, barley, corn, and rice; vegetable protein feeds, for example, those including rapeseeds, beans, and sunflowers as major ingredients; animal protein feeds, for example, blood meal, meat meal, bone meal, and fish meal; and sugar and dairy products, such as animal fats and vegetable fats obtained by mixing dry ingredients composed of milk and whey powders with dry additives and optionally liquefying the mixture with liquid ingredients and ingredients to be liquefied after heating, i.e. lipids, by heating. In addition to these ingredients, the feed composition may further include nutritional supplements, digestion-absorption improvers, growth promoters, prophylactic agents, etc.

The feed composition may be administered alone or in combination with other feed additives in edible carriers to animals.

The feed composition may be used as a top dressing or may be directly mixed with an animal feed. Alternatively, the feed composition may be used separately from a feed. In this case, the feed composition may be easily administered in the form of an oral formulation or in combination with other ingredients by injection or transdermally. In general, the feed composition may be administered in single or divided doses per day, as well known in the art.

When the feed composition is administered separately from an animal feed, the composition may be combined with non-toxic, pharmaceutically acceptable edible carriers to produce either immediate- or sustained-release formulations, as well known in the art. Such edible carriers may be solid or liquid carriers, for example, corn starch, lactose, sucrose, bean flakes, peanut oil, olive oil, sesame oil, and propylene glycol. When the solid carriers are used, the dosage forms of the composition may be tablets, capsules, powders, troches, lozenges, and non-dispersed top dressings. As for the liquid carriers, the dosage forms of the composition may be soft gelatin capsules, syrups, liquid suspensions, emulsions, and solutions. The dosage forms may contain one or more adjuvants, for example, preservatives, stabilizers, wetting agents, emulsifiers or solubilizers The feed composition may be added to the animal feed by soaking, spraying or mixing.

The feed composition may be applied to the diets of a number of animals, including mammals, poultry, and fish. More specifically, the diets may be used for commercially important mammals, for example, pigs, cattle, sheep, goats, laboratory rodents (e.g., rats, mice, hamsters, and gerbils), furry animals (e.g., minks and foxes), zoo animals (e.g., monkeys and apes), and livestock (e.g., cats and dogs). Commercially important poultry species include chickens, turkeys, ducks, geese, pheasants, and quails. Commercially raising fish species, such as trout, may also be included.

When the feed composition is mixed with the animal feed, it is used in an amount of about 1 g to 100 g per 1 kg of the animal feed (on a dry weight basis). After the feed mixture is completely blended, consistent pellets or granules are obtained depending on the degree of pulverization of the ingredients. The blend may be supplied as a mash or may be formed into a desired separate shape for further processing or packaging. At this time, it is preferred that water is added to the animal feed, followed by pelletization, expansion or extrusion. This subsequent process prevents the separation of the feed ingredients during storage. The excess water may be removed by drying.

Yet another aspect of the present invention also provides a cosmetic composition including the broccoli with increased sulforaphane content or a cosmetic composition including a sulforaphane extract produced by the method.

The cosmetic composition of the present invention may be prepared into toners, lotions, essences, creams, and packs.

The broccoli with increased sulforaphane content or the sulforaphane extract produced therefrom may be used in an amount of at least 0.1% by weight, preferably 0.2 to 50% by weight, more preferably 0.3 to 30% by weight, most preferably 0.5 to 10% by weight, based on the weight of each formulation.

The cosmetic composition may further include suitable carriers, excipients or diluents that are usually used in the production of cosmetics.

Examples of the carriers, excipients or diluents include, but are not limited to, purified water, oils, waxes, fatty acids, fatty acid alcohols, fatty acid esters, surfactants, humectants, thickening agents, antioxidants, viscosity stabilizers, chelating agents, buffering agents, and lower alcohols. The cosmetic composition may optionally further include whitening agents, moisturizing agents, vitamins, UV absorbers, perfumes, dyes, and antibacterial agents.

As the oils, there may be used hydrogenated vegetable oils, castor oil, cottonseed oil, olive oil, palm oil, jojoba oil, and avocado oil. As the waxes, there may be used beeswax, spermaceti, carnauba, candelilla, montan, ceresin, liquid paraffin, and lanolin. As the fatty acids, there may be used stearic acid, linoleic acid, linolenic acid, and oleic acid. As the fatty acid alcohols, there may be used cetyl alcohol, octyl dodecanol, oleyl alcohol, panthenol, lanolin alcohol, stearyl alcohol, and hexadecanol. As the fatty acid esters, there may be used isopropyl myristate, isopropyl palmitate, and butyl stearate. Examples of the surfactants include: anionic surfactants, such as sodium stearate, sodium cetyl sulfate, polyoxyethylene lauryl ether phosphate, and sodium N-acyl glutamate; cationic surfactants, such as stearyl dimethyl benzyl ammonium chloride and stearyl trimethyl ammonium chloride; amphoteric surfactants, such as alkylaminoethylglycine hydrochloride and lecithin; and nonionic surfactants, such as glycerin monostearate, sorbitan monostearate, sucrose fatty acid ester, propylene glycol monostearate, polyoxyethylene oleyl ether, polyethylene glycol monostearate, polyoxyethylene sorbitan monopalmitate, polyoxyethylene coconut fatty acid monoethanolamide, polyoxypropylene glycol, polyoxyethylene castor oil, and polyoxyethylene lanolin. Glycerin, 1,3-butylene glycol, and propylene glycol may be used as the humectants. Ethanol and isopropanol may be used as the lower alcohols. Examples of the thickening agents include sodium alginate, sodium caseinate, gelatin agar, xanthan gum, starch, cellulose ethers (e.g., hydroxyethyl cellulose, methyl cellulose, carboxymethyl cellulose, and hydroxypropyl methylcellulose), polyvinylpyrrolidone, polyvinyl alcohol, polyethylene glycol, and sodium carboxymethylcellulose. As the antioxidants, there may be used butylated hydroxytoluene, butylated hydroxyanisole, propyl gallate, citric acid, and ethoxyquin. As the chelating agents, there may be used include disodium edetate and ethanehydroxy diphosphate. As the buffering agents, there may be used citric acid, sodium citrate, boric acid, borax, and disodium hydrogen phosphate.

Advantageous Effects

As described above, the method for preparing broccoli with increased sulforaphane content according to the present invention uses high-voltage pulsed electric field treatment. According to the method of the present invention, broccoli with increased sulforaphane content can be eaten raw or can be chopped to appropriate sizes before eating without the need to crush the broccoli. In addition, sulforaphane can be extracted from the broccoli with increased sulforaphane content. The high-voltage pulsed electric field treatment avoids the need to use a high-pressure vessel, requires a very short treatment time of several seconds to several minutes, and can be performed in both batch and continuous operations. Therefore, the method of the present invention is advantageous in commercialization over techniques known so far. Furthermore, the broccoli with increased sulforaphane content and the sulforaphane extract produced therefrom can be used as an active ingredient of a food, feed or cosmetic composition to exhibit the activities of sulforaphane, including antioxidative and anti-inflammatory activities.

BEST MODE

Figure 1:
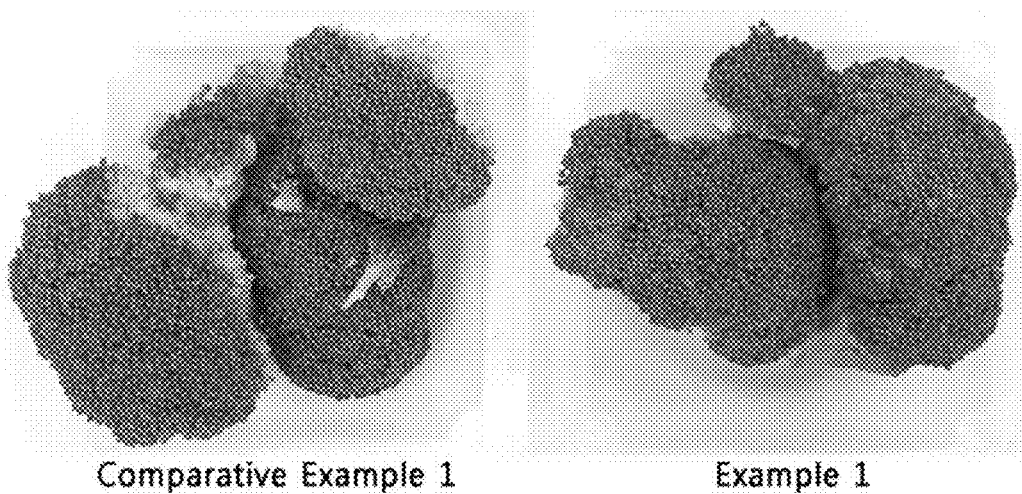
FIG. 1a shows an image of broccoli of Comparative Example 1 (left) and an image of broccoli of Example 1 (right) immediately after high-voltage pulsed electric field treatment.
FIG. 1b shows an image of broccoli of Comparative Example 1 (left) after storage at room temperature for 1 day and an image of broccoli of Example 1 (right) after storage at room temperature for 1 day following high-voltage pulsed electric field treatment.
FIG. 1c shows an image of broccoli of Comparative Example 1 (left) after storage at room temperature for 3 days and an image of broccoli of Example 1 (right) after storage at room temperature for 3 days following high-voltage pulsed electric field treatment.
FIG. 1d shows an image of broccoli of Comparative Example 1 (left) after storage at room temperature for 4 days and an image of broccoli of Example 1 (right) after storage at room temperature for 4 days following high-voltage pulsed electric field treatment.
FIG. 1e shows an image of broccoli of Comparative Example 1 (left) after storage in a cold place for 6 days and an image of broccoli of Example 1 (right) after storage in a cold place for 6 days following high-voltage pulsed electric field treatment.
Figure 2:
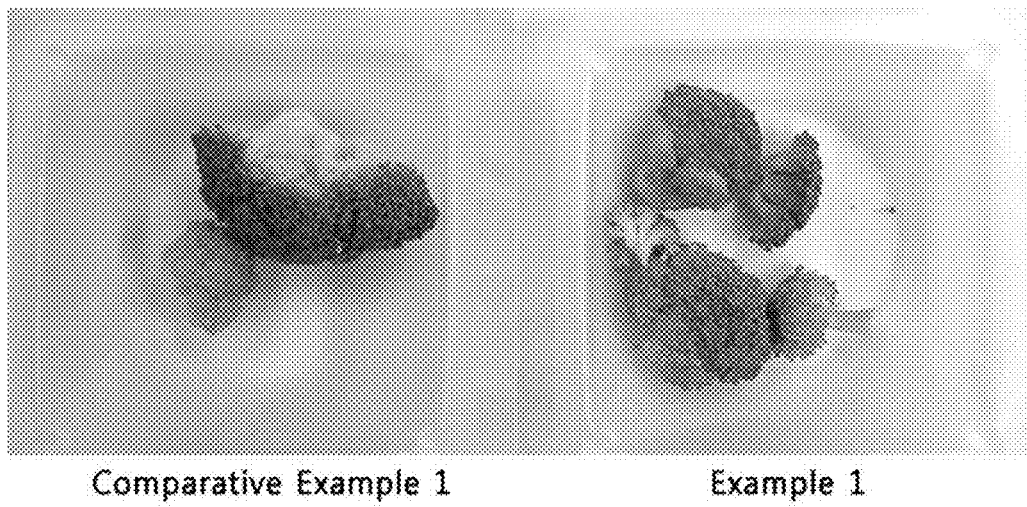
Figure 3:
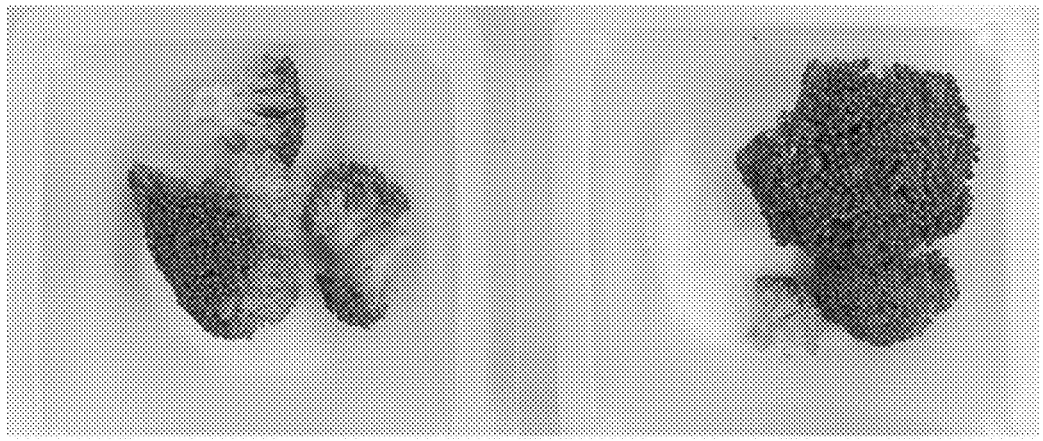
Figure 4:
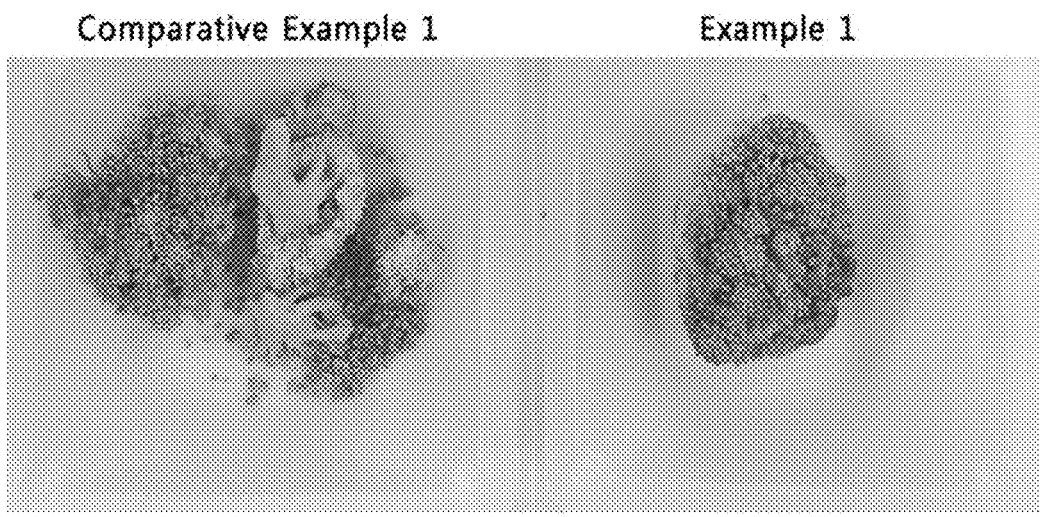
Figure 5:
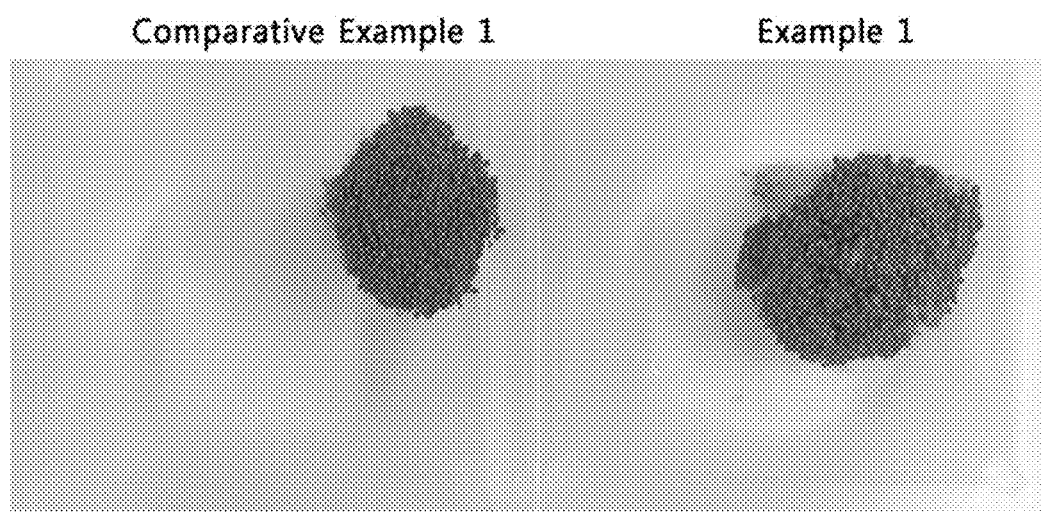

The present invention provides a method for preparing broccoli with increased sulforaphane content, including: introducing broccoli into a batch or continuous type vessel containing a liquid medium; and treating the liquid medium 1 to 50 times with a high-voltage pulsed electric field of 0.1 to 200 kV/cm at a frequency of 1 to 100 Hz for 0.1 to 300 seconds.

Mode for Invention

The present invention will be explained in more detail with reference to the following examples. However, these examples are not intended to limit the scope of the invention.

Fresh broccoli harvested from Jeju-Do, Korea and fresh turnips harvested from Gangwha Island, Korea were purchased and used as samples. An ELCRACK HVP5 apparatus (German Institute of Food Technology, Germany) was used for high-voltage pulsed electric field treatment.

Experimental Example 1: Analysis of Sulforaphane Content of Vegetables Belonging to the Family Brassicaceae The contents of sulforaphane in raw radish, turnip, cabbage, red cabbage, Brussels sprout, broccoli, and cauliflower as vegetables of the family Brassicaceae were analyzed by the following procedure.

A standard solution was prepared using a sulforaphane standard product (90%, Sigma) and was analyzed using UPLC-MS/MS (Waters) to construct a standard calibration curve. 1 g of each sample (on a dry weight basis) was ground in 10 ml of water using a mixer and kept immersed for 2 h such that glucoraphanin was converted to sulforaphane by myrosinase. After a 2-h reaction, the reaction mixture was extracted with 90 ml of methanol with stirring. 1 ml was taken from the extract (100 ml), diluted 10-fold, and analyzed for sulforaphane content by UPLC-MS/MS. The UPLC system was an Acquity UPLC system (Waters corporation, milford, MA) comprised of a binary solvent manager and a sample manager. The MS system was a Waters Quattro Premier XE Tandem MS system (Micromass UK limited). The systems were controlled using Masslynx V4.1 software.

TABLE 1

| Kind | Radish | Turnip | Cabbage | Red cabbage | Broccoli |
|---|---|---|---|---|---|
| Content (mg/100 g dry weight) | 0.7 | 1.5 | 1.9 | 18.6 | 37.4 |

From the results in Table 1, it could be confirmed that red cabbage and broccoli were most suitable for use as sulforaphane sources among the vegetables of the family Brassicaceae.

Experimental Example 2: Analysis of Contents of Sulforaphane Precursor in Broccoli and Red Cabbage To determine the contents of glucoraphanin, a sulforaphane precursor, in the red cabbage and broccoli whose sulforaphane contents were found to be high in Experimental Example 1, the following procedure for simultaneous analysis of sulforaphane and glucoraphanin was established.

A standard solution was prepared using a glucoraphanin standard product (90%, PhytoLab) and was analyzed using UPLC-MS/MS (Waters) to construct a standard calibration curve. 1 g of the sample (on a dry weight basis) was ground in 10 ml of water using a mixer and kept immersed for 2 h such that glucoraphanin was converted to sulforaphane by myrosinase. After a 2-h reaction, 90 ml of ethyl alcohol was added to simultaneously extract glucoraphanin and sulforaphane with stirring, instead of methanol. 1 ml was taken from the extract (100 ml), diluted 10-fold, and analyzed for glucoraphanin and sulforaphane contents by UPLC-MS/MS. The UPLC system was the same as that used in Experimental Example 1. The MS/MS method was carried out by scanning in positive ion mode (MS 178 m/z→Daughter 113.9 m/z) for sulforaphane and in negative ion mode (MS 436 m/z→Daughter 372, 96.9 m/z) for glucoraphanin.

TABLE 2

| Kind | Red cabbage | Broccoli |
|---|---|---|
| Glucoraphanin content (mg/100 g dry weight) | 22.2 | 235.2 |
| Sulforaphane content (mg/100 g dry weight) | 18.6 | 37.4 |

The results in Table 2 show that the sulforaphane content of the red cabbage was about half that of the broccoli but the content of glucoraphanin, a sulforaphane precursor, in the red cabbage was less than one tenth of that in the broccoli. In addition, it was predicted that the conversion of glucoraphanin to sulforaphane in the broccoli would be resulted in a significant increase in sulforaphane content.

Example 1

Inedible parts of fresh broccoli were discarded and the broccoli florets were cut out (50 g at a time). The cut florets were introduced into a water-filled batch type vessel of a high-voltage pulsed electric field treatment system and were once treated at an electric field of 2 kV/cm and a frequency of 10 Hz for 10 sec.

Example 2

The procedure of Example 1 was repeated except that broccoli was once treated at an electric field of 2 kV/cm and a frequency of 20 Hz for 10 sec.

Comparative Example 1

For comparison with the broccoli florets having undergone the high-voltage pulsed electric field treatment, fresh broccoli was used as a control. Inedible parts of the broccoli were discarded and the broccoli florets were cut out (50 g at a time).

Comparative Example 2

Inedible parts of fresh broccoli were discarded and the broccoli florets were cut out (50 g at a time). The cut florets were blanched in boiling water at 100° C. for 1 min.

Comparative Example 3

Inedible parts of fresh broccoli were discarded and the broccoli florets were cut out (50 g at a time). The cut florets were ground using a mixer for 2 min.

Experimental Example 3: Analysis of Sulforaphane Contents

A standard solution was prepared using a sulforaphane standard product (90%, Sigma) and analyzed using UPLC-MS/MS (Waters) to construct a standard calibration curve. Based on the standard calibration curve, each broccoli of Examples 1-2 and Comparative Examples 1-3 was analyzed for sulforaphane content. The analysis was conducted in the same manner as in Experimental Example 1.

TABLE 3

| Kind | Comparative Example 1 | Comparative Example 2 | Comparative Example 3 | Example 1 | Example 2 |
|---|---|---|---|---|---|
| Content (mg/100 g dry weight) | 37.4 | 1.75 | 65.6 | 118.6 | 138.8 |
| Relative proportion (%) | 100.0 | 4.7 | 175.4 | 317.1 | 371.1 |

Experimental Example 4

The number of bacteria in each broccoli of Examples 1-2 and Comparative Examples 1-2 was measured in accordance with the testing method for counting the number of bacteria described in the Korean Food Standards Codex. The results are shown in Table 4. The samples were collected from the broccoli florets where microorganisms are most likely to be viable after washing.

TABLE 4

| kind | Comparative Example 1 | Comparative Example 2 | Example 1 | Example 2 |
|---|---|---|---|---|
| CFU/g | $2.7 \times 10^3$ | $0.97 \times 10^1$ | $2.05 \times 10^1$ | $1.05 \times 10^1$ |

When the broccoli of Comparative Example 2 was blanched in boiling water, the number of bacteria in the broccoli was lowered by ≥99% than that in the fresh broccoli of Comparative Example 2. The effect of the high-voltage pulsed electric field treatment on the sterilization of each broccoli of Examples 1-2 was substantially equal to the sterilization effect in Comparative Example 2.

Experimental Example 5

To predict the storage conditions and shelf life of each broccoli having undergone the high-voltage pulsed electric field treatment, changes in the color of the broccoli of Example 1 and the broccoli of Comparative Example 1 were observed during storage at room temperature (25° C.) and in a refrigerator (5° C.). The images are shown in FIGS. 1a to 1e.

In both the fresh broccoli (Comparative Example 1) and the broccoli having undergone the high-voltage pulsed electric field treatment (Example 1), no browning was observed at room temperature for 3 d but browning occurred on the fourth day. Particularly, the florets of the broccoli of Comparative Example 1 were broken into pieces from the fourth day.

In contrast, both the fresh broccoli (Comparative Example 1) and the broccoli having undergone the high-voltage pulsed electric field treatment (Example 1) did not turn brown under refrigeration conditions even on the sixth day.

From these results, it can be predicted that the shelf life of the broccoli having undergone the high-voltage pulsed electric field treatment will be at least equal to or longer than that of the fresh broccoli.

Example 3

50 g of the broccoli of Example 1 was dried with hot air at 40° C. and powdered.

Example 4

250 ml of an aqueous solution of 70 wt % ethanol was added to 50 g of the broccoli of Example 1. The mixture was pulverized with a homogenizer for 3 min, extracted with stirring at 20° C. for 12 h, concentrated under reduced pressure, and freeze-dried to prepare a sulforaphane extract powder.

Example 5

250 ml of ethyl acetate was added to 50 g of the broccoli florets of Example 1. The mixture was pulverized with a homogenizer for 3 min and extracted with stirring at 20° C. for 1 h. The ethyl acetate layer was concentrated under reduced pressure and freeze-dried to prepare a sulforaphane extract powder.

Experimental Example 6: Analysis of Sulforaphane Contents

The contents of sulforaphane in the broccoli powder of Example 3 and sulforaphane extract powders of Examples 4-5 were analyzed. The analysis was conducted in the same manner as in Experimental Example 1. The results are shown in Table 5.

TABLE 5

| kind | Example 1 | Example 3 | Example 4 | Example 5 |
|---|---|---|---|---|
| Content (mg/100 g solid content) | 1,210 | 445 | 1,830 | 3,580 |

Experimental Example 7

Fresh broccoli florets each was placed in a water-filled batch type treatment vessel of a high-voltage pulsed electric field treatment system. The florets were treated with varying electric fields, frequencies, treatment times, and numbers of treatments. The treated florets were analyzed for sulforaphane contents and were organoleptically evaluated.

20 panelists were requested for the organoleptic evaluation. The evaluation was based on a 9-point scale, where the fresh broccoli of Comparative Example 1 was defined as the highest score (9) and the others were expressed as relative scores. The treatment conditions and the sulforaphane contents are shown in Table 6.

TABLE 6

| kind | Electric field (kV/cm) | Frequency (Hz) | Treatment time (sec) | Number of treatments | Sulforaphane (mg/100 g) | Organoleptic evaluation (9-point scale) |
|---|---|---|---|---|---|---|
| Comparative Example 1 | — | — | — | — | 37.4 | 9 |
| 1-1 | 0.1 | 20 | 10 | 1 | 77.1 | 9 |
| 1-2 | 1.0 | 20 | 10 | 1 | 82.4 | 9 |
| 1-3 | 2.0 | 20 | 10 | 1 | 138.8 | 9 |
| 1-4 | 5.0 | 20 | 10 | 1 | 132.1 | 8 |
| 1-5 | 10.0 | 20 | 10 | 1 | 145.1 | 6 |
| 1-6 | 100.0 | 20 | 10 | 1 | 107.0 | 3 |
| 2-1 | 2.0 | 0.5 | 10 | 1 | 90.5 | 9 |
| 2-2 | 2.0 | 5 | 10 | 1 | 119.2 | 9 |
| 2-3 | 2.0 | 50 | 10 | 1 | 151.4 | 6 |
| 2-4 | 2.0 | 100 | 10 | 1 | 155.0 | 4 |
| 3-1 | 2.0 | 5 | 0.5 | 1 | 66.3 | 9 |
| 3-2 | 2.0 | 5 | 5 | 1 | 58.2 | 9 |
| 3-3 | 2.0 | 5 | 50 | 1 | 121.1 | 7 |
| 3-4 | 2.0 | 5 | 300 | 1 | 103.5 | 4 |
| 3-5 | 2.0 | 5 | 600 | 1 | 99.8 | 2 |
| 4-1 | 2.0 | 5 | 5 | 2 | 49.4 | 9 |
| 4-2 | 2.0 | 5 | 5 | 10 | 88.2 | 8 |
| 4-3 | 2.0 | 5 | 5 | 30 | 82.1 | 6 |
| 4-4 | 2.0 | 5 | 5 | 60 | 56.2 | 4 |

Experimental Example 8

Fresh broccoli florets each was once treated in a liquid medium in a batch type treatment vessel of a high-voltage pulsed electric field treatment system at an electric field of 2 kV/cm and a frequency of 5 Hz for 5 sec. The liquid medium was an aqueous solution of 50 vol % of ethanol, an aqueous solution of 20 vol % of ethanol or 0.5 wt % brine. The sulforaphane contents were analyzed and are shown in Table 7.

TABLE 7

| kind | Preparative Example 3-2 | 50% ethanol | 20% ethanol | 0.5% brine |
|---|---|---|---|---|
| Sulforaphane content (mg/100 g) | 58.2 | 32.2 | 42.1 | 65.5. |

Food compositions containing the broccoli with increased sulforaphane content or the sulforaphane extract produced therefrom according to the present invention were prepared into the following formulations. It should be understood that the proportions of the ingredients in the formulations may be arbitrarily changed depending on the consumers' regional and national preferences, such as classes, nationalities, and purposes of use.

Formulation Example 1: Production of Tablets

| Broccoli powder (Example 3) | 10 mg |
|---|---|
| Corn starch | 100 mg |
| Lactose | 100 mg |
| Magnesium stearate | 2 mg |

The ingredients were mixed together and the mixture was compressed to produce tablets in accordance with a general method known in the art.

Formulation Example 2: Production of Capsules

| | |
|---|---|
| Sulforaphane extract powder (Experimental Example 4) | 10 mg |
| Crystalline cellulose | 3 mg |
| Lactose | 14.8 mg |
| Magnesium stearate | 0.2 mg |

The ingredients were mixed together and the mixture was filled in gelatin capsules to produce capsules in accordance with a general method known in the art.

Formulation Example 3: Production of Powdered Health Functional Food

| | |
|---|---|
| Broccoli powder (Example 3) | 1,000 mg |
| Vitamin mixture | q.s. |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | q.s. |
| Ferrous sulfate | 1.75 mg |
| Zinc oxide | 0.82 mg |
| Magnesium carbonate | 25.3 mg |
| Potassium dihydrogen phosphate | 15 mg |
| Calcium monohydrogen phosphate | 55 mg |
| Potassium citrate | 90 mg |
| Calcium carbonate | 100 mg |
| Magnesium chloride | 24.8 mg |

The vitamin and mineral mixtures were prepared using the ingredients suitable for health functional foods. However, it should be understood that the compositions of the mixtures are provided as preferred embodiments and may be arbitrarily changed. The ingredients were mixed together and the mixture was granulated. In accordance with a general method known in the art, the granules were used to produce a health functional food.

Formulation Example 4: Production of Beverages

| | |
|---|---|
| Sulforaphane extract powder (Example 4) | 1,000 mg |
| Citric acid | 1,000 mg |
| Oligosaccharides | 100 g |
| Plum concentrate | 2 g |
| Taurine | 1 g |
| Purified water | To 900 mL |

In accordance with a general method known in the art, the ingredients were mixed together, heated with stirring at 85° C. for about 1 h, filtered, sealed and sterilized in a sterile 2 L vessel, and kept refrigerated. The resulting solution was used to produce functional beverage compositions.

Cosmetic compositions containing the broccoli with increased sulforaphane content or the sulforaphane extract produced therefrom according to the present invention were prepared into the following formulations. It should be understood that the proportions of the ingredients in the formulations may be arbitrarily changed depending on the consumers' regional and national preferences, such as classes, nationalities, and purposes of use.

Formulation Example 5: Production of Soaps

| | |
|---|---|
| Sulforaphane extract powder (Example 4) | 5 wt % |
| Oils and fats | 75 wt % |
| Sodium hydroxide | 5 wt % |
| Perfume | 10 wt % |
| Purified water | Balance |

In accordance with a general method known in the art, the ingredients were mixed together and the mixture was formulated into soaps.

Formulation Example 6: Production of Lotions

| | |
|---|---|
| Sulforaphane extract powder (Example 4) | 3 wt % |
| L-ascorbic acid-2-phosphate magnesium salt | 1 wt % |
| Water soluble collagen (1% aqueous solution) | 1 wt % |
| Sodium citrate | 0.1 wt % |
| Citric acid | 0.05 wt % |
| Licorice extract | 0.2 wt % |
| 1,3-Butylene glycol | 3 wt % |
| Purified water | Balance |

In accordance with a general method known in the art, the ingredients were mixed together and the mixture was formulated into lotions.

Formulation Example 7: Production of Creams

| | |
|---|---|
| Sulforaphane extract powder (Example 4) | 3 wt % |
| Polyethylene glycol monostearate | 2 wt % |
| Self-emulsified monostearic acid glycerin | 5 wt % |
| Cetyl alcohol | 4 wt % |
| Squalene | 6 wt % |
| Glyceryl tri(2-ethylhexanoate) | 6 wt % |
| Sphingoglycolipid | 1 wt % |
| 1.3-Buthylene glycol | 7 wt % |
| Purified water | Balance |

In accordance with a general method known in the art, the ingredients were mixed together and the mixture was formulated into creams.

Formulation Example 8: Production of Packs

| | |
|---|---|
| Broccoli powder (Example 3) | 2 wt % |
| Polyvinyl alcohol | 13 wt % |
| L-ascorbic acid-2-phosphate magnesium salt | 1 wt % |
| Lauroyl hydroxyproline | 1 wt % |
| Water soluble collagen (1% aqueous solution) | 2 wt % |
| 1,3-Butylene glycol | 3 wt % |
| Ethanol | 5 wt % |
| Purified water | Balance |

In accordance with a general method known in the art, the ingredients were mixed together and the mixture was formulated into packs.

As is apparent from the foregoing, the method for preparing broccoli with increased sulforaphane content according to the present invention uses high-voltage pulsed electric field treatment. According to the method of the present invention, broccoli with increased sulforaphane content can be eaten raw or can be chopped to appropriate sizes before eating without the need to crush the broccoli. In addition, sulforaphane can be extracted from the broccoli with increased sulforaphane content. The broccoli with increased sulforaphane content and the sulforaphane extract produced therefrom can be used as an active ingredient of a food, feed or cosmetic composition to exhibit the activities of sulforaphane, including antioxidative and anti-inflammatory activities.

What is claimed is:

1. A method for preparing broccoli with increased sulforaphane content, comprising: introducing broccoli into a batch or continuous type vessel containing a liquid medium; and treating the liquid medium 1 to 100 times with a high-voltage pulsed electric field of 0.1 to 200 kV/cm at a frequency of 1 to 100 Hz for 0.1 to 300 seconds.

2. The method according to claim 1, wherein the high-voltage pulsed electric field treatment is performed at 0.2 to 20 kV/cm for 1 to 50 seconds.

3. The method according to claim 1, wherein the broccoli being introduced into the vessel is either intact or is chopped into pieces, the broccoli being not subject to pulverization or trituration.

4. The method according to claim 1, wherein the liquid medium is water, ethyl alcohol or a mixture thereof.

5. The method according to claim 1, wherein the broccoli having undergone the high-voltage pulsed electric field treatment is subjected to drying, pulverization, pulverization after drying, or drying after pulverization.

6. Broccoli treated by a high-voltage pulsed electric field method of claim 1, wherein the treated broccoli has increased sulforaphane content, wherein the sulforaphane content after the high-voltage pulsed electric field treatment is higher by at least 100% than its original sulforaphane content before the treatment.

7. A food composition comprising the high-voltage pulsed electric field treated broccoli with increased sulforaphane content according to claim 6.

8. A feed composition comprising the high-voltage pulsed electric field treated broccoli with increased sulforaphane content according to claim 6.

9. A cosmetic composition comprising the high-voltage pulsed electric field treated broccoli with increased sulforaphane content according to claim 6.

10. The high-voltage pulsed electric field treated broccoli according to claim 6, wherein the sulforaphane content after the high-voltage pulsed electric field treatment is higher by at least 200% than its original sulforaphane content before the treatment.

11. The high-voltage pulsed electric field treated broccoli according to claim 6, wherein the sulforaphane content after the high-voltage pulsed electric field treatment is higher by at least 300% than its original sulforaphane content before the treatment.

12. A method for producing a sulforaphane extract from the high-voltage pulsed electric field treated broccoli with increased sulforaphane content according to claim 6, comprising extracting sulforaphane from the high-voltage pulsed electric field treated broccoli with water, an organic solvent, or a mixture thereof.

13. A food composition comprising a sulforaphane extract produced by the method according to claim 12.

14. A feed composition comprising a sulforaphane extract produced by the method according to claim 12.

15. A cosmetic composition comprising a sulforaphane extract produced by the method according to claim 12.

16. A method of increasing sulforaphane content and sterilizing broccoli, comprising: introducing broccoli into a batch or continuous type vessel containing a liquid medium; and treating the liquid medium 1 to 100 times with a high-voltage pulsed electric field of 0.1 to 200 kV/cm at a frequency of 1 to 100 Hz for 0.1 to 300 seconds.

17. A method of extracting sulforaphane from fresh broccoli, comprising:
introducing broccoli into a batch or continuous type vessel containing a liquid medium; and treating the liquid medium 1 to 100 times with a high-voltage pulsed electric field of 0.1 to 200 kV/cm at a frequency of 1 to 100 Hz for 0.1 to 300 seconds;
adding an extraction solvent to the vessel; and
extract with stirring at room temperature for 1 hour.

18. The method of extracting sulforaphane from fresh broccoli according to claim 17, wherein the extraction solvent is selected from the group consisting of water, methanol, ethanol, and a combination thereof.

* * * * *